(12) United States Patent
Lim et al.

(10) Patent No.: US 8,808,642 B2
(45) Date of Patent: Aug. 19, 2014

(54) MICROCHIP

(75) Inventors: Hyun Chang Lim, Seoul (KR); Neon Cheol Jung, Anyang-si (KR); Keun Chang Cho, Seoul (KR)

(73) Assignee: Logos Biosystems, Inc. (KR)

( * ) Notice: Subject to any disclaimer, the term of this patent is extended or adjusted under 35 U.S.C. 154(b) by 0 days.

(21) Appl. No.: 14/237,397

(22) PCT Filed: Nov. 18, 2011

(86) PCT No.: PCT/KR2011/008832
§ 371 (c)(1),
(2), (4) Date: Feb. 6, 2014

(87) PCT Pub. No.: WO2013/027896
PCT Pub. Date: Feb. 28, 2013

(65) Prior Publication Data
US 2014/0178267 A1    Jun. 26, 2014

(30) Foreign Application Priority Data
Aug. 19, 2011    (KR) .................. 10-2011-0082767

(51) Int. Cl.
*G01N 15/06*    (2006.01)
*G01N 33/00*    (2006.01)
*G01N 33/48*    (2006.01)
*B01L 3/00*    (2006.01)

(52) U.S. Cl.
CPC .............................. *B01L 3/502715* (2013.01)
USPC ............ 422/503; 422/50; 422/68.1; 422/502; 436/43

(58) Field of Classification Search
CPC ....... G01N 15/05; G01N 33/00; G01N 33/48; G01N 15/14; G01N 15/1425; G01N 15/1434; G01N 15/1463; G01N 15/147; G01N 15/1475; G01N 15/1484; B01L 3/5027; B01L 3/502707; B01L 3/502715; B01L 3/502776
USPC ........................... 422/68.1, 502, 503; 436/43
See application file for complete search history.

(56) References Cited

U.S. PATENT DOCUMENTS

| | | |
|---|---|---|
| 7,997,831 B2 | 8/2011 | Gilbert et al. |
| 8,057,629 B2 | 11/2011 | Zhou et al. |
| 2005/0272142 A1 | 12/2005 | Horita |

FOREIGN PATENT DOCUMENTS

| | | |
|---|---|---|
| JP | 2006030160 | 2/2006 |
| KR | 200230956 | 5/2001 |

(Continued)

OTHER PUBLICATIONS

International Search Report—PCT/KR2011/008832 dated Sep. 25, 2012.

(Continued)

*Primary Examiner* — Brian J Sines
(74) *Attorney, Agent, or Firm* — Cantor Colburn LLP

(57) ABSTRACT

Disclosed is a microchip. The microchip of the present invention is characterized by comprising: a first plate; and a second plate coupled to the first plate to form a channel, wherein the first plate comprises: a channel cover part; a first connection part spaced apart from the outer periphery of the channel cover part by a certain distance; and a tensile strength generation connecting part for mutually connecting the channel cover part and the first connection part so that the channel cover part elastically contacts the channel region formed on the second plate when the first plate is coupled to the second plate. According to the present invention, the channel cover part forming the channel elastically contacts the channel region formed on the second plate, thereby providing a microchip capable of providing a channel having a stable structure.

15 Claims, 10 Drawing Sheets

(56) References Cited

FOREIGN PATENT DOCUMENTS

| KR | 1020060134942 | 12/2006 |
| KR | 1020080059426 | 6/2008 |
| KR | 1020100047977 | 5/2010 |
| KR | 1020110115483 | 10/2011 |

OTHER PUBLICATIONS

Korean Notice of Allowance—Korean Application No. 10-2011-0082767 issued on Feb. 21, 2013 citing KR1020100047977, KR1020110115483, JP2006030160 and KR200230956.

MICROCHIP

TECHNICAL FIELD

The present disclosure relates to a microchip, and more particularly to a microchip in which a channel covering unit forming a channel comes in elastically close contact with a channel forming area of a second plate so as to provide a channel of a stable structure.

BACKGROUND ART

Generally, the microchip including a structure of a channel form has been widely used for purposes of cultivating cells, counting various particles including cells, and causing or measuring a reaction of fluid in in biology, medicine, environmental engineering, and food engineering fields.

For example, there is a product group of channel slides, manufactured by Ibidi Gmbh, Germany, as a case in that the microchip with the channel structure is used in the cultivation of the cells. This has shown that a micro channel is formed between two plates and an upper plate is made from a gas-permeable plastic, so as to achieve a purpose of cultivating the cells in the channel.

Further, in the case that the number or concentration of cells is measured, a channel shaped structure is used in a clinical laboratory and a biological laboratory. At this time, the concentration of the particles is indicated by the number of particles per unit volume. Accordingly, in order to measure the accurate number or the concentration of the particles, the volume within the microchip must be constantly maintained. Particularly, a hemocytometer which is a microchip generally used for a purpose of counting the cells is a device for defining a fixed volume, in which a height jaw prescribing an accurate height of a lower plate and an upper plate is made through a glass process and a cover glass is placed on the height jaw to maintain a precise height.

As described above, a process of moving, reacting, mixing and detecting fluid using the micro channel is a technology very generally used in a micro fluidics field. That is, in the micro fluidics field, the above mentioned purpose will be achieved by adding various types of structures within the channel. In any case, manufacturing of a microchip in which two or more plates are precisely adhered is a previous requirement to form a channel structure including fluid.

Especially, in an application field requiring that a solution in the channel has a desired volume, for example in a field of manufacturing the hemocytometer, it is an essential requirement to precisely form a height of the channel in correspondence to the desired purpose.

Hereinafter, the microchip will be described in more detail with reference to FIG. 18. Here, FIG. 18 is a perspective view illustrating a microchip according to a conventional art.

Referring to FIG. 18, the conventional microchip 10 includes an upper plate 11 on which an injection port 14 and a discharging port 15 are formed to be spaced at a predetermined distance from each other, and a lower plate 12 coupled to a lower surface of the upper plate 11 so that a channel 13 is formed between the upper plate 11 and the lower plate 12.

In the conventional microchip 10 according to the above-mentioned structure, when a sample is injected in the injection port 14, the sample is filled within the channel.

However, with the conventional microchip, since the upper plate and the lower plate are adhered by a solvent, a supersonic wave, and the like, to form the channel, or the channel is formed by using a film lamination, in which transparent upper and lower plates are adhered in turn to an upper portion and a lower portion of the channel, there is a problem in that a manufacturing process is complicated and difficult.

Further, there are problems in that since a process of manufacturing the conventional microchip is complicated and difficult, automatic equipment is required to mass-manufacture the microchip and a manufacturing cost increases due to a process of adhering the upper plate to the lower plate.

Furthermore, in the conventional microchip, when a solvent is unevenly coated or surfaces of the upper plate and the lower plate are uneven in an operation of adhering the upper plate to the lower plate, the upper plate is not completely adhered to the lower plate, resulting in a leakage of a solution. Also, since a deviation of height in the adhered surfaces of the upper plate and the lower plate is generated, there is a problem in that it is difficult to provide the channel with a desired volume.

In addition, the conventional microchip has a disadvantage in that the solvent used for the adhesion may react with a bio-substance in the channel so as to induce an undesired biological or chemical reaction.

DISCLOSURE OF THE INVENTION

Technical Problems

The present disclosure is made to solve the above-mentioned problems in the conventional art, and an aspect of the present disclosure is to provide a microchip in which a channel covering unit forming a channel is in elastically close contact with a channel forming area of a second plate so as to provide the channel with a stable structure.

Means To Solve The Problem

In accordance with an aspect of the present disclosure, a microchip is provided. The microchip includes: a first plate; and a second plate coupled with the first plate so as to form a channel, wherein the first plate comprises: a channel covering portion; a first adhesion portion spaced at a desired distance from an outer periphery of the channel covering portion; and a tension generating connector configured to connect the channel covering portion to the first adhesion portion so that the channel covering portion is in elastically close contact with a channel forming area of the second plate when the first plate is coupled with the second plate.

The tension generating connector may include a plurality of tension generating connectors which are spaced at a constant distance from one another between the channel covering portion and the first adhesion portion.

The tension generating connector may have a thinner thickness that the channel covering portion and the first adhesion portion.

The tension generating connector may be prepared on upper regions of opposed vertical surfaces of the channel covering portion and the first adhesion portion.

The tension generating connector may be configured to be in the form of a curved line or a straight line to connect the channel covering portion and the first adhesion portion with each other, in order to increase a relative connection distance in comparison to a manner of connecting the channel covering portion to the first adhesion portion by a shortest distance.

The second plate includes: a second adhesion formed at an edge of the second plate and coupled with the first adhesion portion; a bottom portion depressed in a center area of an upper surface under the second adhesion portion; a channel portion protruding from the bottom portion; and a supporting wall protruding from the bottom portion at a position spaced at a desired distance from the channel portion to form a closed loop and having a thickness thicker than the channel portion so that the an edge area of a lower surface of the channel covering portion is in close contact with the supporting wall to form a channel between the channel portion and the channel covering portion.

The supporting wall may have the thickness thicker than the second adhesion portion so that the lower surface of the channel covering portion is supported by an upper surface of the supporting wall when the first adhesion portion and the second adhesion portion are coupled with each other.

The supporting wall may be formed in any one shape selected from a polygonal shape, a circular shape and an elliptical shape.

A reservoir portion primarily receiving the solution may be formed between the supporting wall and the channel portion.

The first adhesion portion and the second adhesion portion may be coupled by a coupling means.

The coupling means may include: one or more hooks protruding from the lower surface of the first adhesion portion and spaced at a constant distance from one another along a periphery of the first adhesion portion; and one or more hook insertion recesses formed at positions corresponding to the hooks on the second adhesion portion so that the hooks are inserted in the hook insertion recesses respectively.

Each hook may include: a body portion having a circular shape in section; and one or more deformable ribs protruding from a periphery of the body portion and spaced at a constant distance from one another along the periphery of the body portion.

The coupling means may include: one or more posts protruding from the lower surface of the first adhesion portion and spaced at a constant distance from one another along a periphery of the first adhesion portion; and one or more post insertion recesses formed at positions corresponding to the posts on the second adhesion portion so that the posts are inserted in the post insertion recesses respectively.

Each post has one end at which a latching jaw is configured to have elasticity and to protrude radially from a periphery of the post.

The first adhesion and the second adhesion are coupled with each other by the coupling means, and then a coupling portion or the channel portion may be sealed by a solvent bonding or an ultrasonic bonding.

Advantageous Effects

According to the present disclosure, the channel covering unit formed on the first plate comes in elastically close contact with the supporting wall of the second plate by means of the tension generating connector so that the channel covering unit and the supporting wall can maintain contact bonding.

BEST MODE FOR CARRYING OUT THE INVENTION

Mode For The Invention

Hereinafter, the preferred embodiments of the present disclosure will be described in detail with reference to the accompanying drawings. In the description of the present disclosure, the description of well-known functions or structures will be omitted in order to make the subject matter of the present disclosure clear.

Further, although the microchip of the present disclosure will be described hereinafter under an assumption in that it is used as a microchip for counting particles or cells in a sample, the scope of the present disclosure is not limited thereto.

A term "microchip" used in the present disclosure refers to a structure which is formed of two or more substrates or plates, and has a channel or a space prescribed by two adjacent substrates or plates among them, in which a fluid or a sample for a test or an analysis may be filled in the channel or the space.

Accordingly, the "microchip" of the present disclosure may be used for various purposes of the test or the analysis in various fields such as a biotechnology, food engineering, chemical engineering, a medicine and the like.

Figure 1:
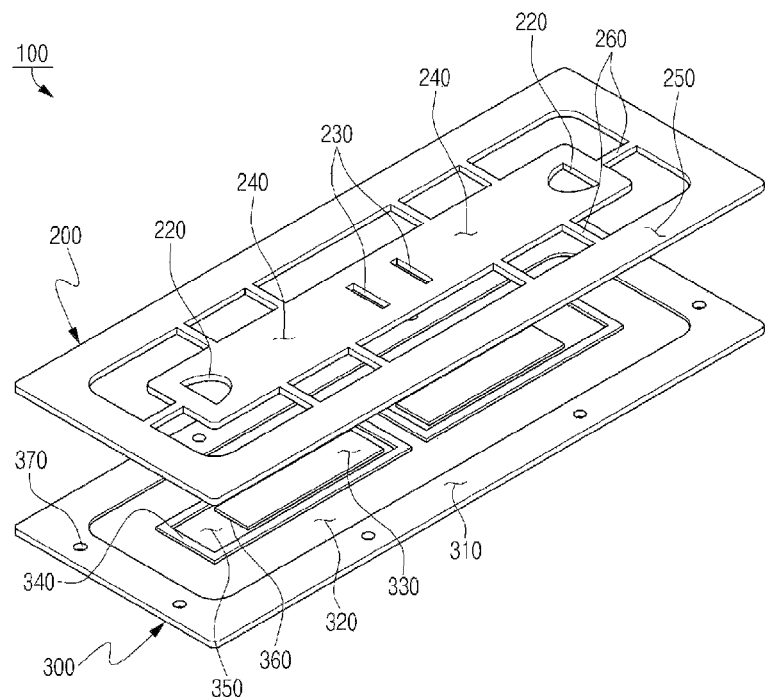
FIG. 1 is an exploded perspective view illustrating a microchip according to an embodiment of the present disclosure.
Figure 2:
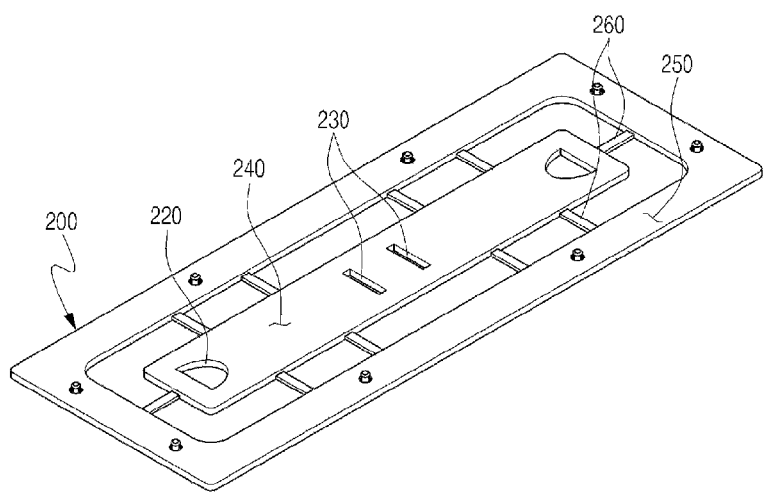
FIG. 2 is a perspective view illustrating a first plate of the microchip of FIG. 1.
Figure 3:
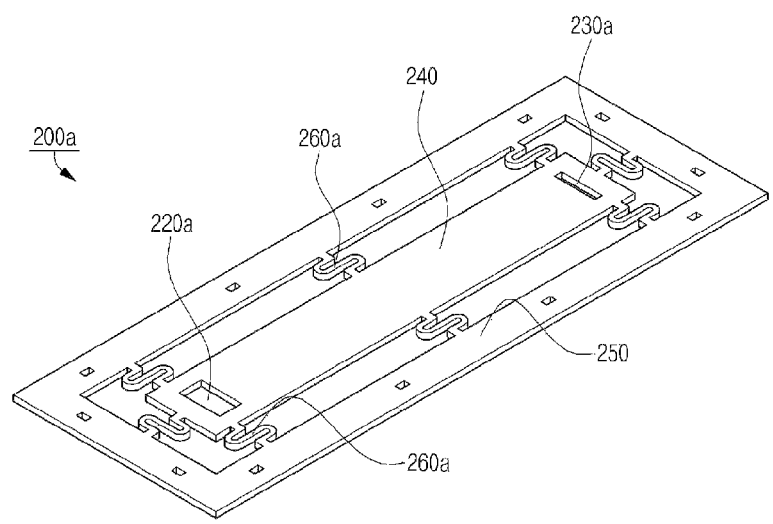
FIGS. 3, 4, 5, 6, 7 and 8 are perspective views illustrating a first plate according to another embodiment of the present disclosure.
Figure 4:
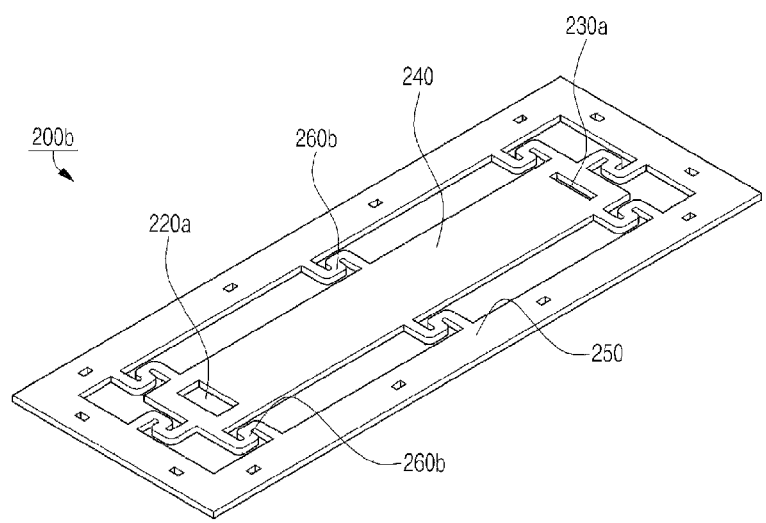
Figure 5:
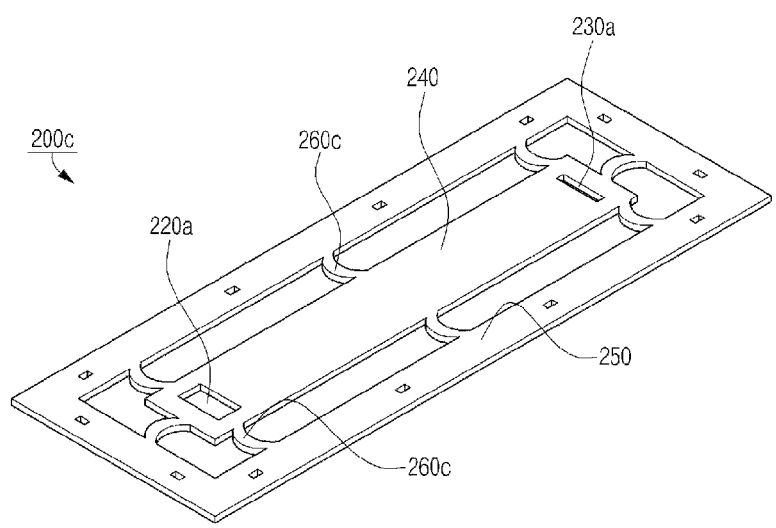
Figure 6:
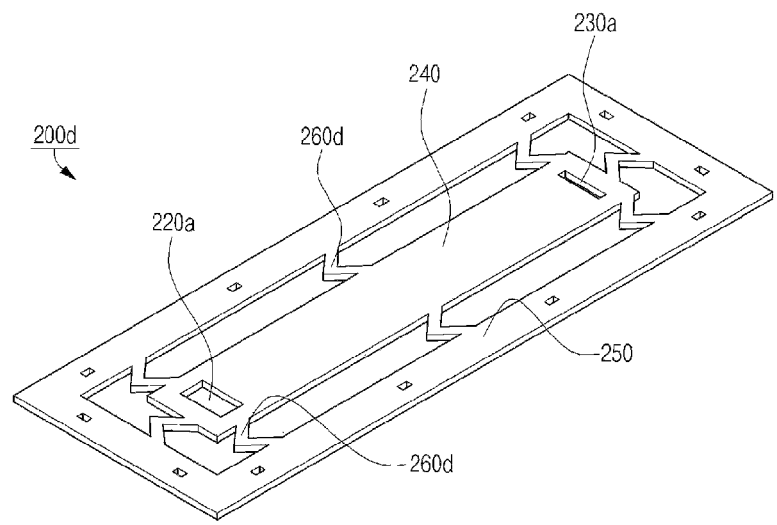
Figure 7:
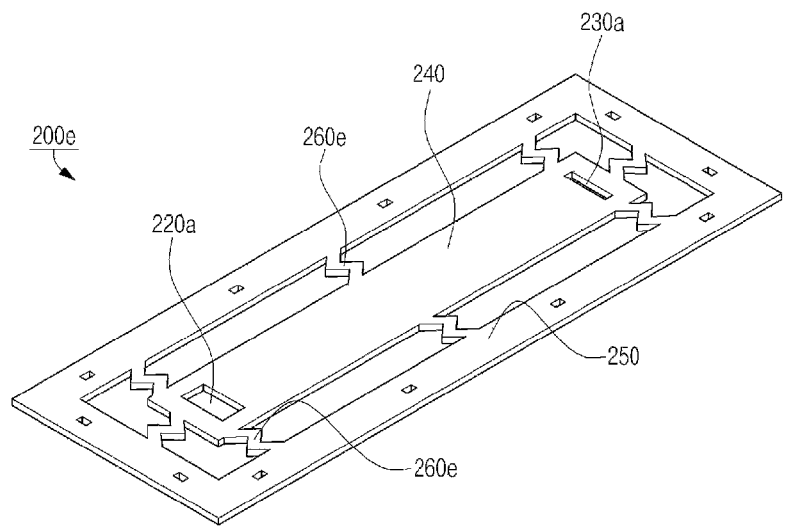
Figure 8:
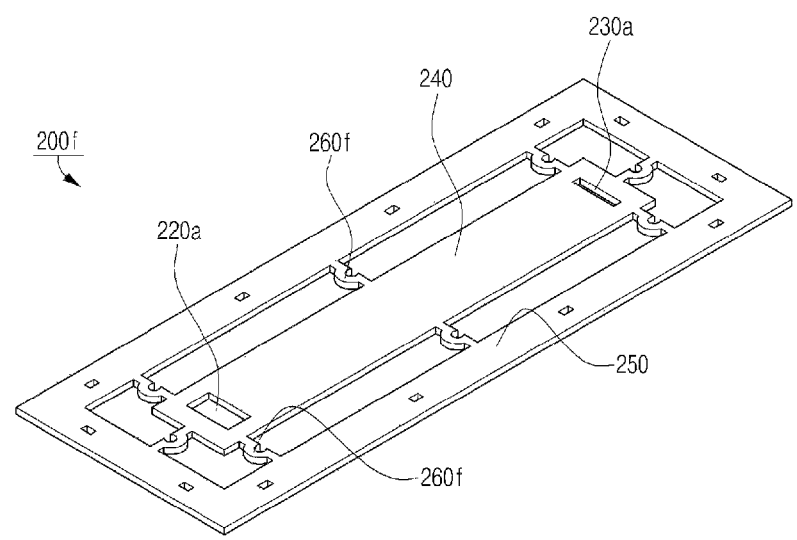
Figure 9:
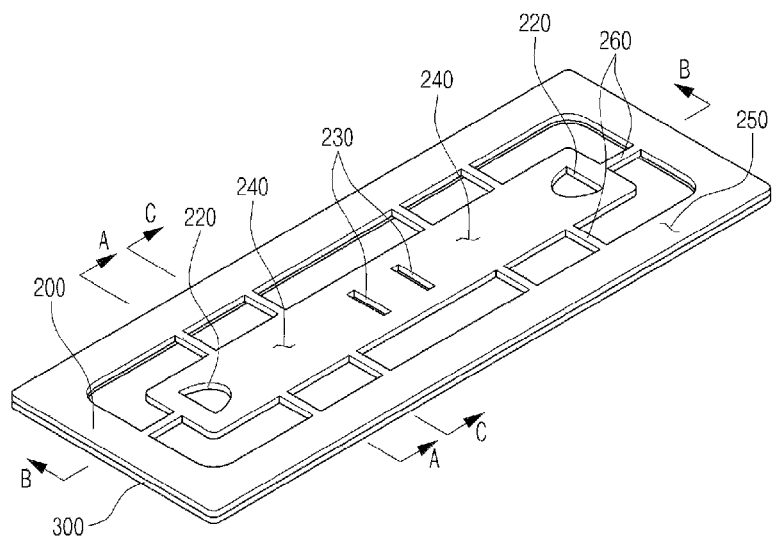
FIG. 9 is a perspective view illustrating the microchip of FIG. 1 which is assembled.
Figure 10:
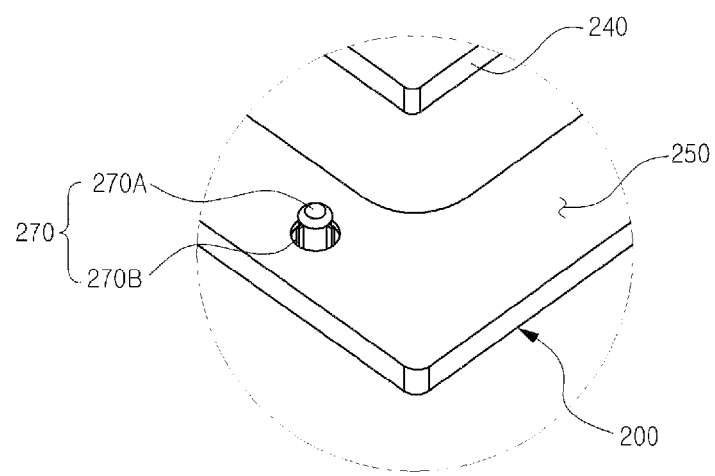
FIGS. 10, 11 and 12 are a perspective view and partially enlarged sectional views illustrating a hook of the microchip of FIG. 1.
Figure 11:
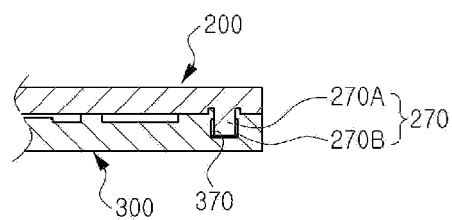
Figure 12:
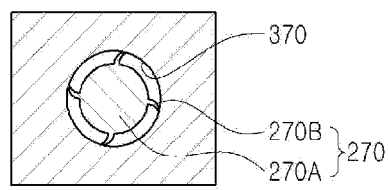

FIG. 1 is an exploded perspective view of the microchip according to the embodiment of the present disclosure, FIG. 2 is a perspective view illustrating a first plate of the microchip of FIG. 1, FIGS. 3, 4, 5, 6, 7 and 8 are perspective views illustrating a first plate according to other embodiments of the present disclosure, FIG. 9 is a perspective view illustrating the microchip of FIG. 1 which is assembled, FIGS. 10, 11 and 12 are a perspective view and partially enlarged sectional views illustrating a hook of the microchip of FIG. 1, and FIGS. 13, 14 and 15 are sectional views illustrating the microchip, taken along lines of A-A, B-B and C-C of FIG. 9, respectively.

Referring to the drawings, the microchip 100 according to an embodiment of the present disclosure includes a first plate 200 which has a channel covering portion 240 formed with an injection port 220 and a discharging port 230, and a second plate 300 provided with a channel portion 330 and a supporting wall 340 and coupled with the first plate 200 so that a channel 400 is formed between the channel portion 330 and the channel covering portion 240.

In the embodiment, the first plate 200 and the second plate 300 are made of a transparent synthetic resin material, but the scope of the present disclosure is not limited by the material of the first plate 200 and the second plate 300.

Figure 17:
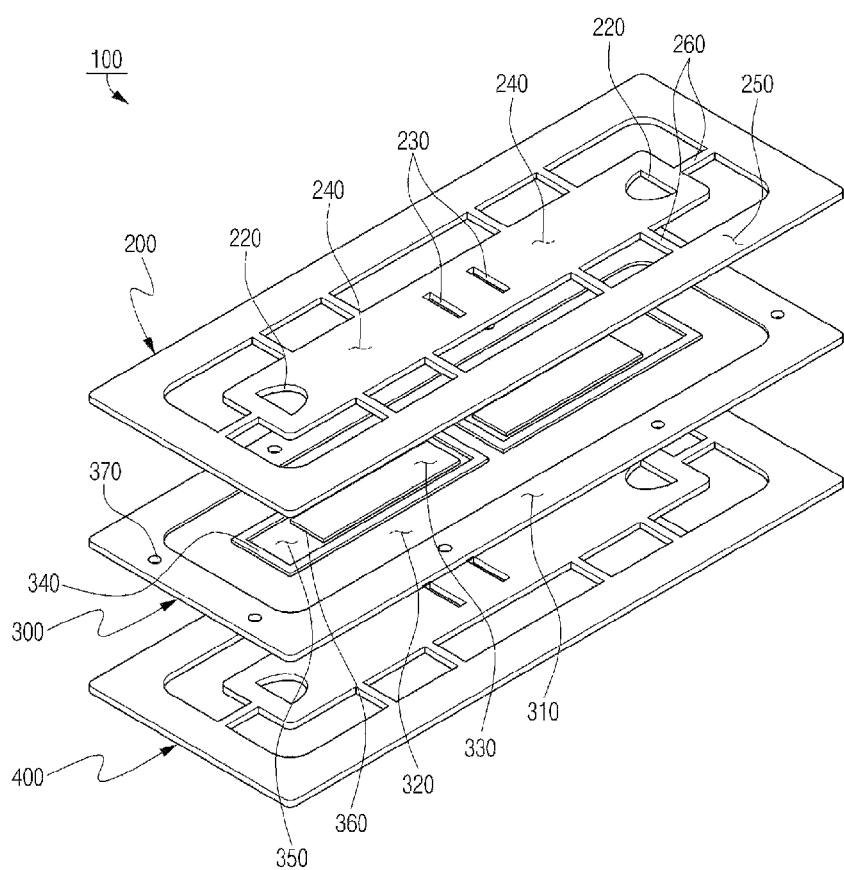
FIG. 17 is an exploded view illustrating the microchip of FIG. 1 according to still another embodiment of the present disclosure.
Figure 18:
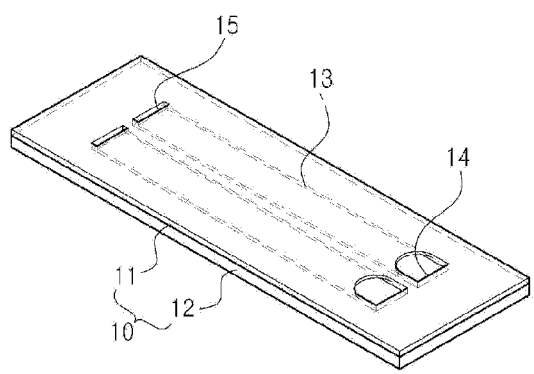
FIG. 18 is a perspective view illustrating a microchip according to the conventional art.

Further, if necessary, the microchip 100 of the present disclosure may further include a third plate 400 coupled with the second plate 300 at a position corresponding to the first plate 200 (see FIG. 17). In this case, the first plate 200 has a structure, which is substantially identical to that formed on an upper surface, formed on a lower surface. The first plate 200 and the third plate 400 are coupled with each other in a substantially identical manner to that of coupling the first plate 100 and the second plate 300 (however, in FIG. 17, the coupling manner of the first plate 200 and the third plate 400 is omitted in order to concisely show the drawing). The detailed description of the coupling manner will be omitted because the coupling manner is sufficiently described in the description of the present embodiment below.

The first plate 200 includes the channel covering portion 240 in which the injection port 220 for injecting a sample (solution) and the discharging port 230 for discharging air from the channel 400 when the sample is injected through the injection port 220 are formed to be spaced at a desired distance from each other, and a first adhesion portion 250 spaced at a predetermined distance from an outer periphery of the channel covering portion 240.

In addition, the first plate 200 further includes a plurality of tension generating connectors 260 which connect the first adhesion portion 250 with the channel covering portion 240.

The tension generating connectors 260 generate tensile force for pulling the channel covering portion 240 in four directions so that the channel covering portion 240 is in elastically close contact with the supporting wall 340 of the second plate, and has a thinner thickness than the channel covering portion 240 and the first adhesion portion 250.

The reason that the tension generating connectors 260 have the thinner thickness than thicknesses of the channel covering portion 240 and the first adhesion portion 250 is to enable the tension generating connectors to sufficiently generate tensile force when the first plate 200 is coupled with the second plate 300.

If the tension generating connectors 260 have the thickness identical to or thicker than the thicknesses of the channel covering portion 240 and the first adhesion portion 250, the thickness of the tension generating connectors 260 must be adjusted because there may be a problem in that the tensile force cannot be sufficiently generated when the first plate 200 is coupled with the second plate 300.

Of course, the thickness of the tension generating connectors 260 may be changed if necessary.

Figure 15:
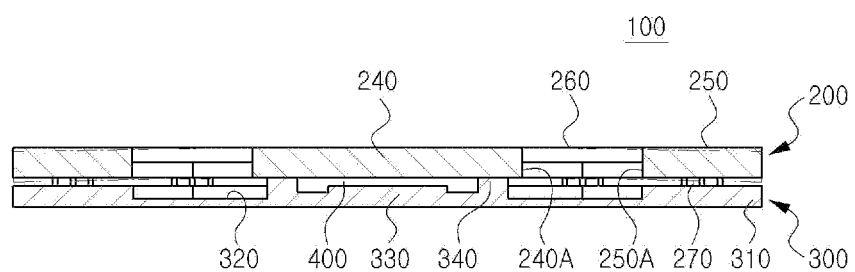

Each tension generating connector 260 is formed at an upper region on vertical and opposite surfaces 240A and 250A of the channel covering portion 240 and the first adhesion portion 250, as shown in FIG. 15.

Thus, in the state that the channel covering portion 240 is in contact with the supporting wall 340, when the first adhesion portion 250 and the second adhesion portion 310 are coupled with each other by means of a hook 270 which is a coupling means, each tension generating connector 260 generates the tensile force while being deformed downwardly, so that the channel covering portion 240 is in elastically close contact with the supporting wall 340.

If the tension generating connectors 260 are formed at a lower region of the vertical surfaces 240A and 250A, the tension generating connectors 260 are not sufficiently deformed although the first adhesion portion 250 and the second adhesion portion 310 are coupled with each other. Accordingly, the tensile force is not generated at all, or insufficiently generated.

Considering the above description, the tension generating connectors 260 of the present embodiment may be provided on both ends of each which are integrally formed at the upper region of the vertical surfaces 240A and 250A, respectively, as shown in FIG. 15.

Although it is not shown in the drawings, further, the tension generating connector 260 may be formed to have only a thinner thickness than the channel covering portion 240 and the first adhesion portion 250, instead of forming the plurality of the tension generating connectors. In this case, both ends of the tension generating connector 260 are integrally formed at the upper regions of the vertical surfaces 240A and 250A, and this structure enables the tensile force to be sufficiently applied to the channel covering portion 240 as described above.

As shown in FIGS. 3, 4, 5, 6, 7 and 8, on the other hand, the tension generating connectors 260a, 260b, 260c, 260d, 260e and 260f according to another embodiment of the present disclosure may be provided in the form of plural curved lines or straight lines between the channel covering portion 240 and the first adhesion portion 250.

Here, the curved line and the straight line mean members with a desired volume and a curved or straight shape.

The tension generating connectors 260a, 260b, 260c, 260d, 260e and 260f with various shapes as shown in FIGS. 3, 4, 5, 6, 7 and 8 have a relatively long length in comparison with the tension generating connector 260 in the straight form of connecting the channel covering portion 240 with the first adhesion portion 250 by the shortest distance as shown in FIG. 2.

As described above, the tension generating connectors 260a, 260b, 260c, 260d, 260e and 260f with the relatively long length have an advantage of more elastically providing the tensile force when the first adhesion portion 250 and the second adhesion portion 310 are adhered by means of the hook 270.

Further, the tension generating connectors 260a, 260b, 260c, 260d, 260e and 260f shown in FIGS. 3, 4, 5, 6, 7 and 8 may have a thickness identical to those of the channel covering portion 240 and the first adhesion portion 250, differently from the tension generating connector 260 shown in FIG. 2.

As shown in FIGS. 3, 4, 5, 6, 7 and 8, on the other hand, each of the first plates 200a, 200b, 200c, 200d, 200e and 200f has one injection port 220a and one discharging port 230a formed therein, and also the second plate 300 described later has one channel (not shown) formed therein.

However, the first plates 200a, 200b, 200c, 200d, 200e and 200f may have a pair of the injection port 220a and the discharging port 230a formed to be similar to the first plate 200 shown in FIG. 1, and also the second plate may have a pair of channels formed therein.

Besides, the injection port 220a and the discharging port 230a are not limited with relation to shapes and the numbers thereof, and may be formed in various shapes. The injection port 220a and the discharging port 230a may be formed in plural pairs as well as in one pair.

Figure 13:
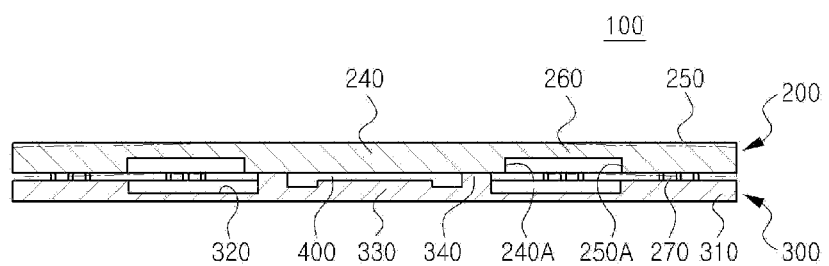
FIGS. 13, 14 and 15 are sectional views illustrating the microchip, taken along lines of A-A, B-B and C-C, respectively.
Figure 14:
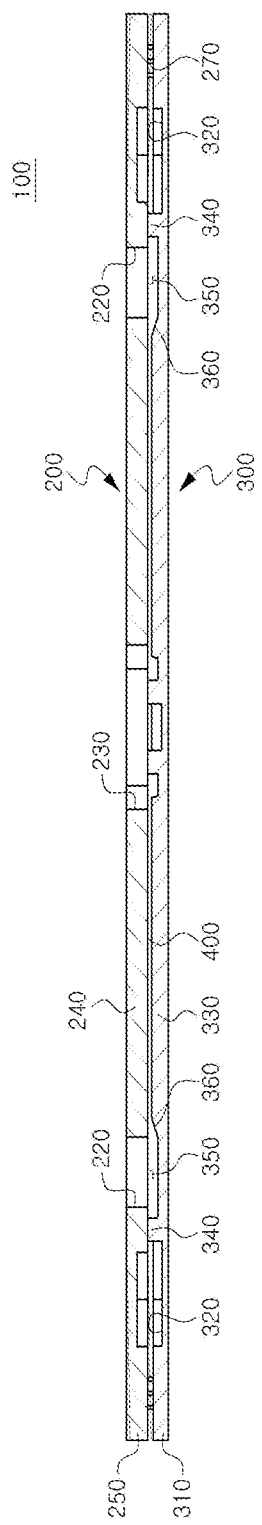

As shown in FIGS. 1 and 13, on the other hand, the second plate 300 is coupled with the first plate 200 to form a channel 400 therebetween, and includes a second adhesion 310 formed at an edge to correspond to the first adhesion 250 and adhered to the first adhesion 250, a bottom portion 320 depressed at a desired depth in a center region on an upper surface, a channel portion 330 protruding upwardly from the bottom portion 320, and a supporting wall 340 protruding from the bottom portion at a position spaced at a desired distance from the channel portion 330 and having a closed type diagram.

The channel portion 330 has a long length corresponding to a distance between the injection port 220 and the discharging portion 230 formed at both ends thereof. Since the channel portion 330 is formed to protrude from a depressed bottom portion 320 of the second plate, the microchip 100 of the present embodiment does not have a thicker whole thickness than a necessary thickness even though the first plate 100 and the second plate 300 are coupled with each other.

The supporting wall 340 is in close contact with an edge area of the lower surface of the channel covering portion 240 and has a thicker thickness than that of the channel portion 330 so that the channel 400 is formed between the channel portion 330 and of the lower surface of the channel covering portion 240.

When the first adhesion portion 240 is adhered to the second adhesion portion 310, the supporting wall 340 is formed to have a thicker thickness than that of the second adhesion portion 310.

In the embodiment, further, the supporting wall 340 has a rectangular shape so as to enclose the channel portion 330 formed in a lengthwise direction, but the scope of the present disclosure is not limited by the shape of the supporting wall 340.

That is, according to another embodiment of the present disclosure, the supporting wall 340 may be formed in the shape selected from a polygon, a circle, and an ellipse if close adhesion and contact bonding between the supporting wall 340 and the channel covering portion 240 are highly maintained.

On the other hand, the second plate 300 further includes a reservoir portion 350 which firstly receives a solution injected through the injection port 220, and an incline surface 360 of the channel portion 330 inclined to the reservoir portion 350.

The reservoir portion 350 is formed at a position corresponding to the injection port 220 formed in the first plate 200 between the supporting wall 340 and the channel portion 330 on the second plate, to firstly receive the solution, and the incline surface 360 is formed at a side of the channel portion 330 so that the solution received in the reservoir portion 350 easily moves to an upper surface of the channel portion 330, i.e., the channel 400.

According to the structure, the solution injected through the injection port 220 is firstly received in the reservoir portion 350, and then smoothly moves to the channel 400 along the incline surface 360 by a capillary action.

On the other hand, the microchip 100 further includes a coupling means for coupling the first plate 200 with the second plate 300 in a one-touch manner.

As shown in FIGS. 10, 11 and 12, the coupling means is provided to the first adhesion portion 250 and the second adhesion portion 310, in which a plurality of hooks 270 are formed on a lower surface of the first adhesion portion 250, and hook insertion recesses 370 are formed at positions corresponding to the hooks 270 on the second adhesion portion 310.

According to the structure, the hooks 270 are inserted in the hook insertion recesses 370, so that the first plate 200 and the second plate 300 are coupled with each other in the one-touch insertion manner.

As shown in FIGS. 10 and 11, on the other hand, each hook 270 includes a body portion 270A protruding from the lower surface of the first adhesion portion 250 and having a circular shape in section, and at least one deformable rib 270B formed along and protruding from a periphery of the body portion 270A.

Meanwhile, the hook insertion recesses are depressed in the second adhesion portion 310.

The deformable rib 270B is deformed while being inserted between the body portion 270A and the hook insertion recess 370 when the body portion 270A is inserted into the hook insertion recess 370, so as to rigidly fix the body portion 270A to the hook insertion recess 370.

Of course, the coupling means of the embodiment may be substituted with a post 280 of the embodiment described later, and may be modified in various forms of coupling the first plate 200 with the second plate 300 according to still another embodiment of the present disclosure.

Hereinafter, use of the microchip 100 of the embodiment will be briefly described.

Firstly, in order to construct one microchip 100 by coupling the first plate 200 with the second plate 300, the first adhesion 250 is in close contact with the second adhesion 310 and the hooks 270 provided as the coupling means are inserted in the hook insertion recesses 370, respectively.

That is, the first adhesion portion 250 and the second adhesion portion 310 are pressed from outside so that the hooks 270 of the first adhesion portion 250 are inserted in the hook insertion recesses 370 of the second adhesion 310 respectively.

In this process, when the body portion 270A of the hook 270 is inserted into the hook insertion recess 370, the deformable ribs 270B protruding from the peripheral surface of the body portion 270A are deformed and elastically interposed between the body portion 270A and the hook insert recesses 370, so that the body portion 270A is forcibly inserted in the hook insertion recess 370. Thus, the first adhesion portion 250 and the second adhesion portion 310 are rigidly and easily coupled with each other.

When the first adhesion portion 250 and the second adhesion portion 310 are coupled through the above-mentioned process, an edge of the lower surface of the channel covering portion 240 is in close contact with the upper surface of the supporting wall 340.

That is, since the tension generating connector 260, which is thinner than the channel covering portion 240 and the first adhesion portion 250, is connected to the upper regions of the vertical surfaces 240A and 250A so as to connect the channel covering portion 240 to the first adhesion portion 250, the tension generating connector 260 generates the tensile force to pull the channel covering portion 240 in four directions, and simultaneously generates an elastic force to make the lower surface of the channel covering portion 240 be in close contact with the supporting wall 340.

Therefore, the channel covering portion 240 can be in elastically close contact with the supporting wall 340 by means of the tension generating connector 260.

As a result, the channel 400 with a desired volume is formed between the channel covering portion 240 and the channel portion 330. That is, since the channel covering portion 240 is pulled by the tensile force of the tension generating connectors 260 in the four directions while being in close contact with the supporting wall 340, there is no deformation in the channel covering portion 240, and a contact surface of the channel covering portion 240 with the supporting wall 340 is even. Accordingly, the channel 400 formed therein has a constant volume.

In the case that the microchip 100 of the embodiment is used to count particles or cells in the solution, a sample solution is injected through the injection port 220. At this time, the injected solution is temporarily received and then moves along the incline surface 360 to the channel 400 formed between the channel covering portion 240 and the channel portion 330 by the capillary action.

At this time, since the channel 330 is spaced from the supporting wall 340, the solution of the channel 400 is prevented from leaking between the channel covering portion 240 and the supporting wall 340.

In the microchip 100 of the embodiment, the channel covering portion 240 formed on the first plate 200 is made to be in elastically close contact with the supporting wall 340 of the second plate 300 by means of the tension generating connector 260, so that the channel covering portion 240 and the supporting wall 340 maintain the contact bonding. Thus, there are advantages in that the solution received in the channel 400 is prevented from leaking, and the channel 400 has an even height.

Figure 16:
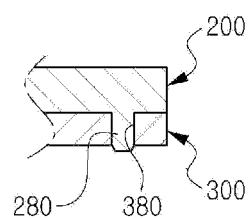
FIG. 16 is a partially enlarged sectional view illustrating a post of the microchip of FIG. 1 according to another embodiment of the present disclosure.

FIG. 16 is a partially enlarged sectional view illustrating a post of the microchip of FIG. 1 according to another embodiment of the present disclosure.

The microchip shown in FIG. 16 has an identical structure to the microchip 100 of the above-mentioned embodiment, but has a difference in the coupling means. Accordingly, hereinafter, only the coupling means will be described.

The coupling means of the microchip (not shown) according to the embodiment includes a plurality of posts 280 which protrude and are spaced at a constant distance from one another along an edge of the lower surface of the first adhesion portion 250, and a plurality of insertion recesses 380 which are formed in the second adhesion portion 310 at positions corresponding to the posts 280 so that the posts 280 pass through and are inserted in the recesses 380.

The posts 280 are provided to protrude along the edge of the lower surface of the first adhesion portion 250 and are inserted in the post recesses 380 which are formed along the edge of the second adhesion portion 310, thereby coupling the first plate 200 and the second plate 300 with each other.

Of course, although they are not shown, the deformable ribs 270B identical to those formed on the periphery of the body portion 270A of the hook 270 may be additionally prepared on the peripheral surface of the post 280, so as to enhance coupling force.

Further, although it is not shown, an elastic latching jaw is prepared at an end of the hook 270 or the post 280 so that the hook 270 or post 280 is latched after being inserted in the hook insertion recess 370 or the post insertion recess 380.

Furthermore, the first adhesion portion 250 and the second adhesion portion 310 are coupled with each other by means of the coupling means in the form of the hook 270 or the post 280, and then a coupling portion or the channel 330 may be tightly sealed by a solvent bonding or an ultrasonic bonding.

Although the specific embodiment of the present disclosure has been described and shown above, the present disclosure is not limited to the described embodiment. It is obvious to those skilled in the art that various changes and modifications can be implemented without departing from the scope and spirit of the present disclosure. Accordingly, the changed example or the modified example should not be individually understood in view of the technical spirit or a view point of the present disclosure, and it is regarded that they belong to the claims of the present disclosure.

The invention claimed is:

1. A microchip comprising:
a first plate; and
a second plate coupled with the first plate so as to form a channel,
wherein the first plate comprises: a channel covering portion; a first adhesion portion spaced at a desired distance from an outer periphery of the channel covering portion; and a tension generating connector configured to connect the channel covering portion to the first adhesion portion so that the channel covering portion is in elastically close contact with a channel forming area of the second plate when the first plate is coupled with the second plate.

2. The microchip as claimed in claim 1, wherein the tension generating connector includes a plurality of tension generating connectors which are spaced at a constant distance from one another between the channel covering portion and the first adhesion portion.

3. The microchip as claimed in claim 2, wherein the tension generating connector has a thinner thickness than the channel covering portion and the first adhesion portion.

4. The microchip as claimed in claim 3, wherein the tension generating connector is prepared on upper regions of opposed vertical surfaces of the channel covering portion and the first adhesion portion.

5. The microchip as claimed in claim 2, wherein the tension generating connector is configured to be in the form of a curved line or a straight line to connect the channel covering portion and the first adhesion portion with each other, in order to increase a relative connection distance in comparison to a manner of connecting the channel covering portion to the first adhesion portion by a shortest distance.

6. The microchip as claimed in claim 1, wherein the second plate comprises: a second adhesion portion formed at an edge of the second plate and coupled with the first adhesion portion; a bottom portion depressed in a center area of an upper surface under the second adhesion portion; a channel portion protruding from the bottom portion; and a supporting wall protruding from the bottom portion at a position spaced at a desired distance from the channel portion to form a closed loop and having a thickness thicker than the channel portion so that the an edge area of a lower surface of the channel covering portion is in close contact with the supporting wall to form a channel between the channel portion and the channel covering portion.

7. The microchip as claimed in claim 6, wherein the supporting wall has the thickness thicker than the second adhesion portion so that the lower surface of the channel covering portion is supported by an upper surface of the supporting wall when the first adhesion portion and the second adhesion portion are coupled with each other.

8. The microchip as claimed in claim 6, wherein the supporting wall is formed in any one shape selected from a polygonal shape, a circular shape and an elliptical shape.

9. The microchip as claimed in claim 5, wherein a reservoir portion primarily receiving the solution is formed between the supporting wall and the channel portion.

10. The microchip as claimed in claim 6, wherein the first adhesion portion and the second adhesion portion are coupled by a coupling means.

11. The microchip as claimed in claim 10, wherein the coupling means comprises: one or more hooks protruding from the lower surface of the first adhesion portion and spaced at a constant distance from one another along a periphery of the first adhesion portion; and one or more hook insertion recesses formed at positions corresponding to the hooks on the second adhesion portion so that the hooks are inserted in the hook insertion recesses respectively.

12. The microchip as claimed in claim 11, wherein each hook comprises: a body portion having a circular shape in section; and one or more deformable ribs protruding from a periphery of the body portion and spaced at a constant distance from one another along the periphery of the body portion.

13. The microchip as claimed in claim 10, wherein the coupling means comprises: one or more posts protruding from the lower surface of the first adhesion portion and spaced at a constant distance from one another along a periphery of the first adhesion portion; and one or more post insertion recesses formed at positions corresponding to the posts on the second adhesion portion so that the posts are inserted in the post insertion recesses respectively.

14. The microchip as claimed in claim 13, wherein each post has one end at which a latching jaw is configured to have elasticity and to protrude radially from a periphery of the post.

15. The microchip as claimed in claim 10, wherein the first adhesion and the second adhesion are coupled with each other by the coupling means, and then a coupling portion or the channel portion is sealed by a solvent bonding or an ultrasonic bonding.

\* \* \* \* \*